(12) United States Patent
Heckerman

(10) Patent No.: US 10,568,756 B1
(45) Date of Patent: Feb. 25, 2020

(54) FEMALE URINE DEVICE

(71) Applicant: OUTSTANDING INNOVATIONS, LLC, Lakeside, MT (US)

(72) Inventor: Brad B. Heckerman, Lakeside, MT (US)

(73) Assignee: OUTSTANDING INNOVATIONS, LLC, Kalispell, MT (US)

( * ) Notice: Subject to any disclaimer, the term of this patent is extended or adjusted under 35 U.S.C. 154(b) by 0 days.

(21) Appl. No.: 16/120,552

(22) Filed: Sep. 4, 2018

(51) Int. Cl.
A61F 5/44 (2006.01)
A61F 5/455 (2006.01)

(52) U.S. Cl.
CPC .......... A61F 5/4556 (2013.01); A61F 5/4553 (2013.01)

(58) Field of Classification Search
CPC .............................. A61F 5/4556; A61F 5/4553
USPC ......................................................... 604/329
See application file for complete search history.

(56) References Cited

U.S. PATENT DOCUMENTS

| | | | |
|---|---|---|---|
| 3,964,111 A * | 6/1976 | Packer .................. | A61F 5/4556 4/144.4 |
| 3,995,329 A * | 12/1976 | Williams ................ | A61F 5/455 4/144.3 |
| 4,023,216 A * | 5/1977 | Li ......................... | A61F 5/4556 4/144.3 |
| 4,528,703 A | 7/1985 | Kraus | |
| 5,330,453 A * | 7/1994 | Cornellier ..................... | 604/329 |
| D356,865 S | 3/1995 | Ivie | |
| 5,408,703 A | 4/1995 | Cicio | |
| 5,743,948 A | 4/1998 | Cicio | |
| 5,893,176 A | 4/1999 | Magiera et al. | |
| 5,966,748 A | 10/1999 | Young et al. | |
| 6,434,757 B1 | 8/2002 | Filsouf | |
| 6,547,771 B2 | 4/2003 | Robertson et al. | |
| D577,435 S | 9/2008 | Ivie et al. | |
| 8,221,369 B2 | 7/2012 | Parks et al. | |
| 8,235,956 B2 | 8/2012 | Block | |
| 2009/0056003 A1* | 3/2009 | Ivie ........................ | A61F 5/4556 4/144.3 |
| 2011/0028944 A1 | 2/2011 | Chiu et al. | |
| 2012/0210502 A1* | 8/2012 | Baham .................. | A61F 5/4556 4/144.3 |

FOREIGN PATENT DOCUMENTS

| | | |
|---|---|---|
| AU | 8089682 A | 9/1982 |
| EP | 0073203 A | 3/1983 |

(Continued)

Primary Examiner — Andrew J Mensh
(74) Attorney, Agent, or Firm — Heslin Rothenberg Farley & Mesiti P.C.

(57) ABSTRACT

A female urine device includes a shell and a resilient liner. The shell includes a bottom wall, a first sidewall, a second sidewall and a rear wall integrally connected to define an inner chamber. A forward opening is defined by forward ends of the walls. An upper rim is defined by upper ends of the walls. The resilient liner is disposed on the inner chamber. The liner extends forward past the forward opening of the shell to form a spout portion of the liner. At least one thumb rest is disposed on a sidewall of the shell and extends perpendicularly therefrom. The at least one thumb rest is sized to receive a thumb of a female and is operable as a fulcrum to enable the female to leverage the rim into sealing engagement with the female's genitalia when the female urine device is in use.

28 Claims, 6 Drawing Sheets

(56) References Cited

FOREIGN PATENT DOCUMENTS

| | | | |
|---|---|---|---|
| FR | 8104021 | A1 | 9/1982 |
| IT | 1149781 | B | 9/1982 |
| WO | 8202831 | A1 | 9/1982 |

\* cited by examiner

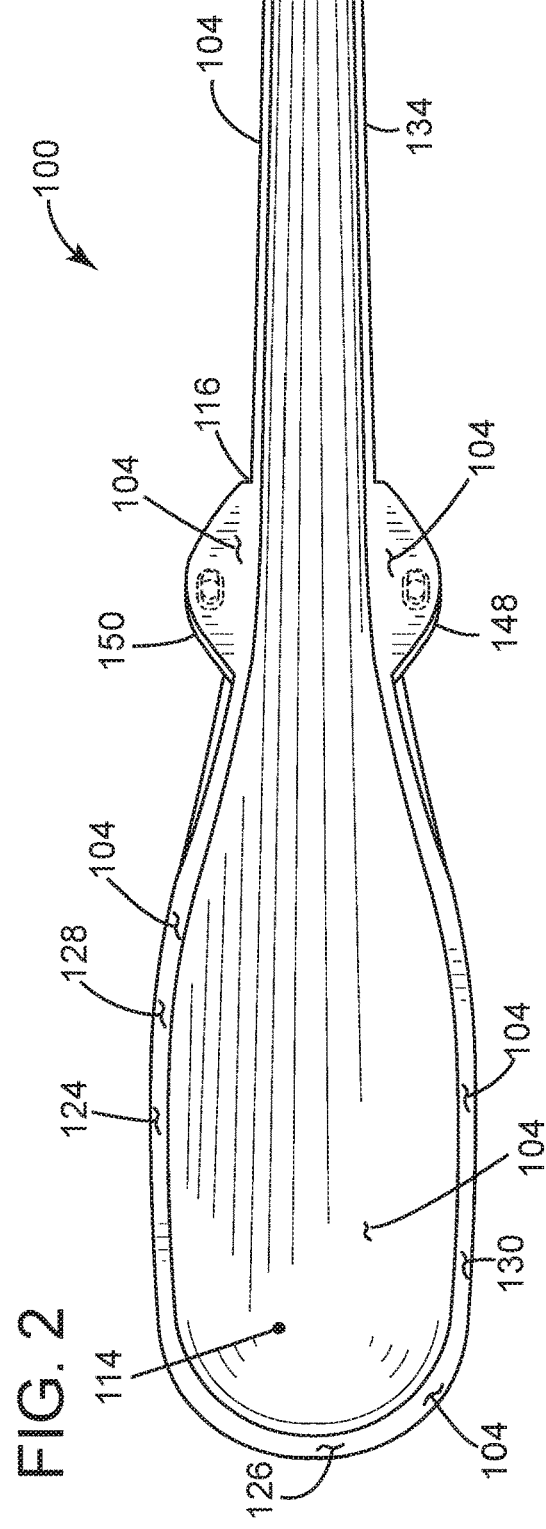
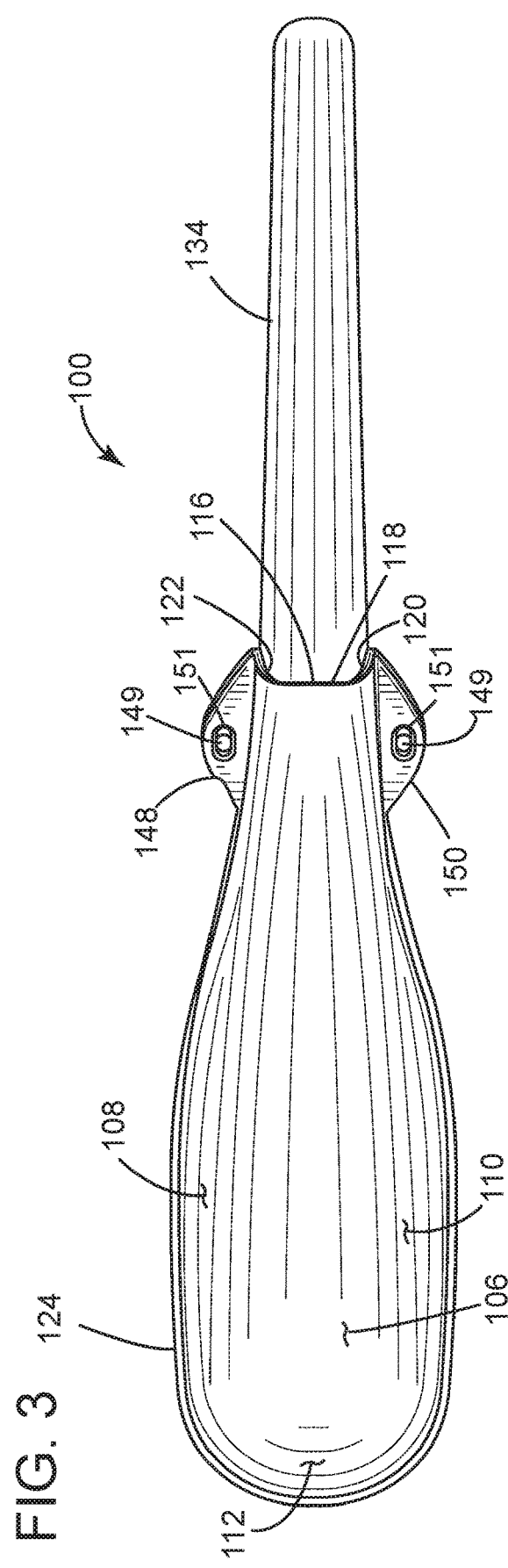

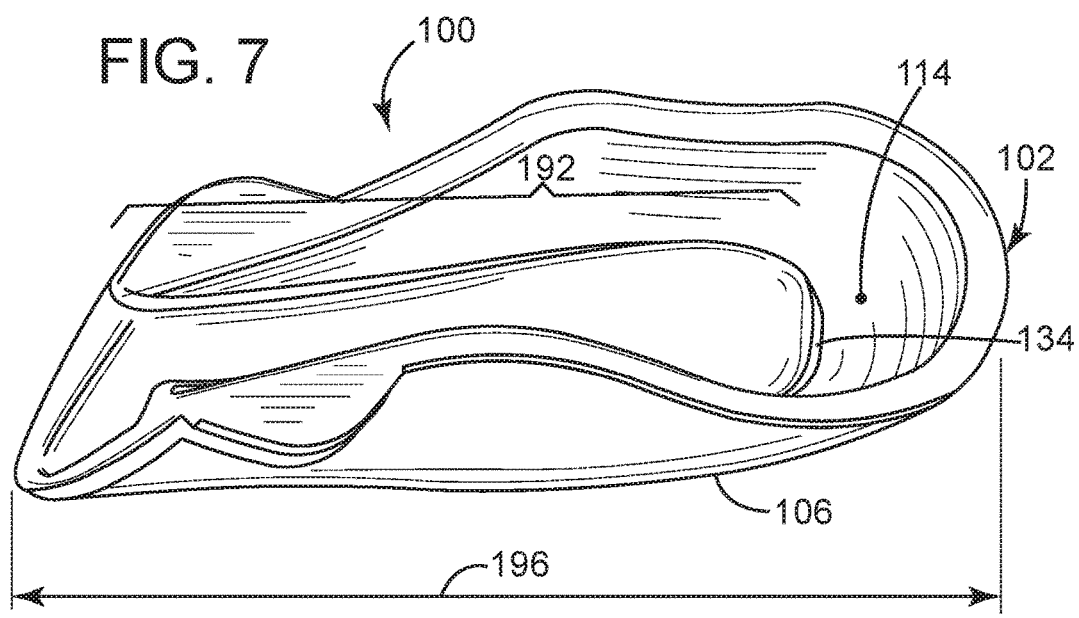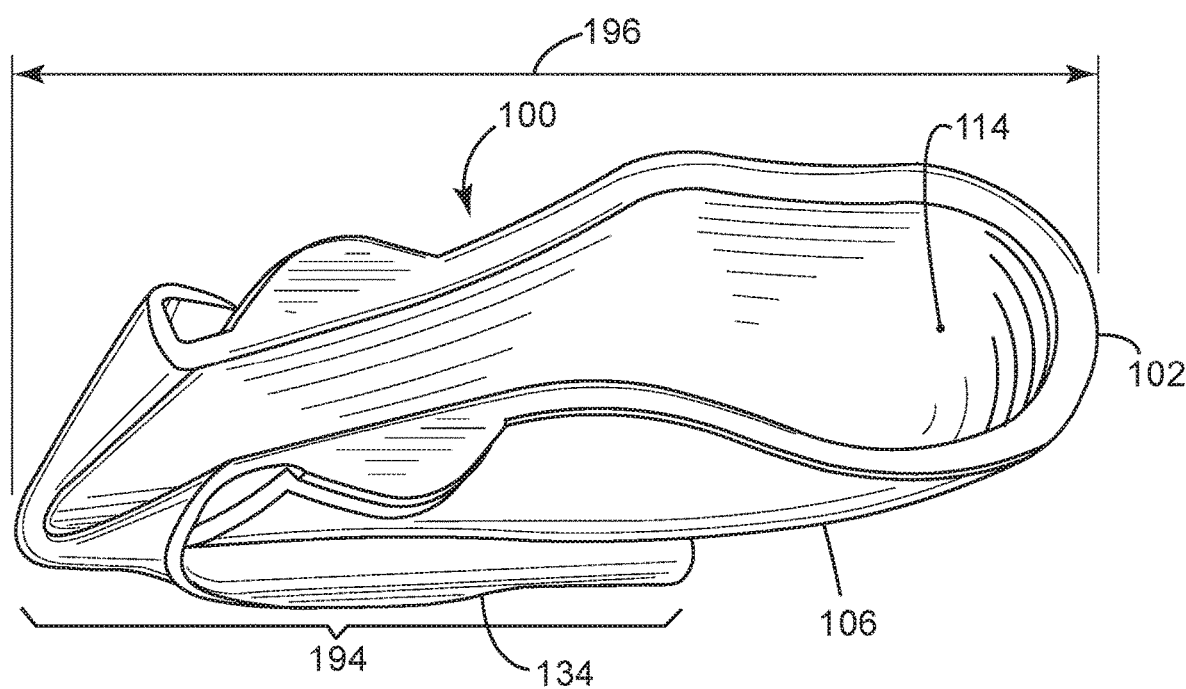

FEMALE URINE DEVICE

TECHNICAL FIELD

The present disclosure relates to female urine devices. More specifically, the disclosure relates to female urine devices which enable a female to urinate while standing.

BACKGROUND

In order to urinate, a female typically must disrobe and sit or squat. However, on many occasions, sitting or squatting to urinate is inconvenient or difficult to do. For example, when hiking over rough outdoor terrain, disrobing may unnecessarily expose a female to harsh weather conditions such as cold wind, snow and heavy rain, or to insects such as mosquitos and black flies. Additionally, disrobing and squatting can be problematic for a female in outdoor public areas, such as parks, which often do not have adequate restroom facilities. In the event there are public restrooms or toilets, many may be dirty and unsanitary. Moreover, certain medical conditions may compound the problem by making it difficult or painful to squat or sit.

Prior art female urine devices which allow a female to urinate while standing (i.e., stand-to-pee devices) may help to alleviate the problem. However, such devices often have several design limitations. For example, prior art female urine devices may leak during urination if not properly positioned and sealed against a female's anatomy.

Often such prior art devices are made of rigid materials throughout to prevent collapsing, and therefore leaking, during use. However, such rigid devices may require an uncomfortable amount of pressure against the female's body in order to seal and prevent leakage. Alternatively, if the prior art device is made of a soft or flexible material, the devices may inadvertently collapse during use when a sealing pressure is applied.

Additionally, such prior art urine devices may be too bulky or too long to conveniently or inconspicuously carry around. This is especially the case when the prior art device is composed of a rigid material throughout.

Further, if the prior art devices are made compact for purposes of easy storage and transport, they may not direct the discharging urine far enough away from a female's body to prevent splashing on one's body or clothing. Such prior art devices may require the female to substantially disrobe to prevent undesirable splashing on one's clothing, which defeats the purpose of a stand-to-pee device.

Accordingly, there is a need for a female urine device that enables a female to conveniently stand during urination without having to disrobe to prevent splashing on one's clothing. Further, there is a need for such a device to be compact enough to easily carry and inconspicuously conceal when not in use, yet long enough to direct discharging urine well away from the body when in use. Moreover, there is a need for a female urine device to be easily and comfortably positioned and sealed against a female's anatomy to greatly reduce the possibility of leakage during use, yet rigid enough to prevent collapsing during use.

BRIEF DESCRIPTION

The present disclosure offers advantages and alternatives over the prior art by providing a female urine device that is composed of a shell and a resilient liner. The shell forms a trough shaped inner chamber upon which the resilient liner is disposed. The liner extends past a forward opening in the shell to form a spout portion. The shell includes thumb tabs to enable a female to easily leverage the urine device into sealing engagement with the female's genitalia without collapsing. The shell includes an upper rim with a concave shaped designed for a comfortable anatomical fit against the female's genitalia when in use. The resilient spout portion has an extended position that is long enough to direct urine away from the body without splashing onto a female's clothing. The resilient spout portion has at least one folded position that enables the female urine device to be more compactly stored.

A female urine device in accordance with one or more aspects of the present disclosure includes a shell and a resilient liner. The shell includes a bottom wall, a first sidewall, a second sidewall and a rear wall integrally connected to define a trough shaped inner chamber. A forward opening of the shell is defined by forward ends of the walls. An upper rim of the shell is defined by upper ends of the walls. The resilient liner is disposed on the inner chamber. The liner extends forward past the forward opening of the shell to form a spout portion of the liner. At least one thumb rest is disposed on a sidewall of the shell and extends perpendicularly therefrom. The at least one thumb rest is sized to receive a thumb of a female and is operable as a fulcrum to enable the female to leverage the rim of the shell into sealing engagement with the female's genitalia when the female urine device is in use.

An alternative female urine device in accordance with one or more aspects of the present disclosure includes a shell and a resilient liner. The shell includes a bottom wall, a first sidewall, a second sidewall and a rear wall integrally connected to define a trough shaped inner chamber. A forward opening of the shell is defined by forward ends of the walls. An upper rim of the shell is defined by upper ends of the walls. The resilient liner is disposed on the inner chamber. The liner extends forward past the forward opening of the shell to form a spout portion of the liner. The spout portion has an extended position and at least one folded position. When the urine device is in use, the upper rim is operable to engage a female's genitalia, the liner covered inner chamber is operable to receive urine from the female's urethral orifice and the spout portion is in its extended position to direct the urine away from the female's body. When the urine device is not in use, the spout portion is operable to be folded into its at least one folded position against the shell for purposes of storage of the urine device.

An alternative female urine device in accordance with one or more aspects of the present invention includes a shell and a resilient liner. The shell includes a bottom wall, a first sidewall, a second sidewall and a rear wall integrally connected to define a trough shaped inner chamber. A forward opening is defined by forward ends of the walls. An upper rim is defined by upper ends of the walls. A resilient liner is disposed on the inner chamber. The liner extends forward past the forward opening of the shell to form a spout portion of the liner. A portion of the upper rim has a concave shaped curve designed to anatomically fit against the female's genitalia.

DRAWINGS

The disclosure will be more fully understood from the following detailed description taken in conjunction with the accompanying drawings, in which:

FIG. 2 depicts a top view of the example of the female urine device of FIG. 1 according to aspects described herein;

FIG. 3 depicts a bottom view of the example of the female urine device of FIG. 1 according to aspects described herein;

Figure 1:
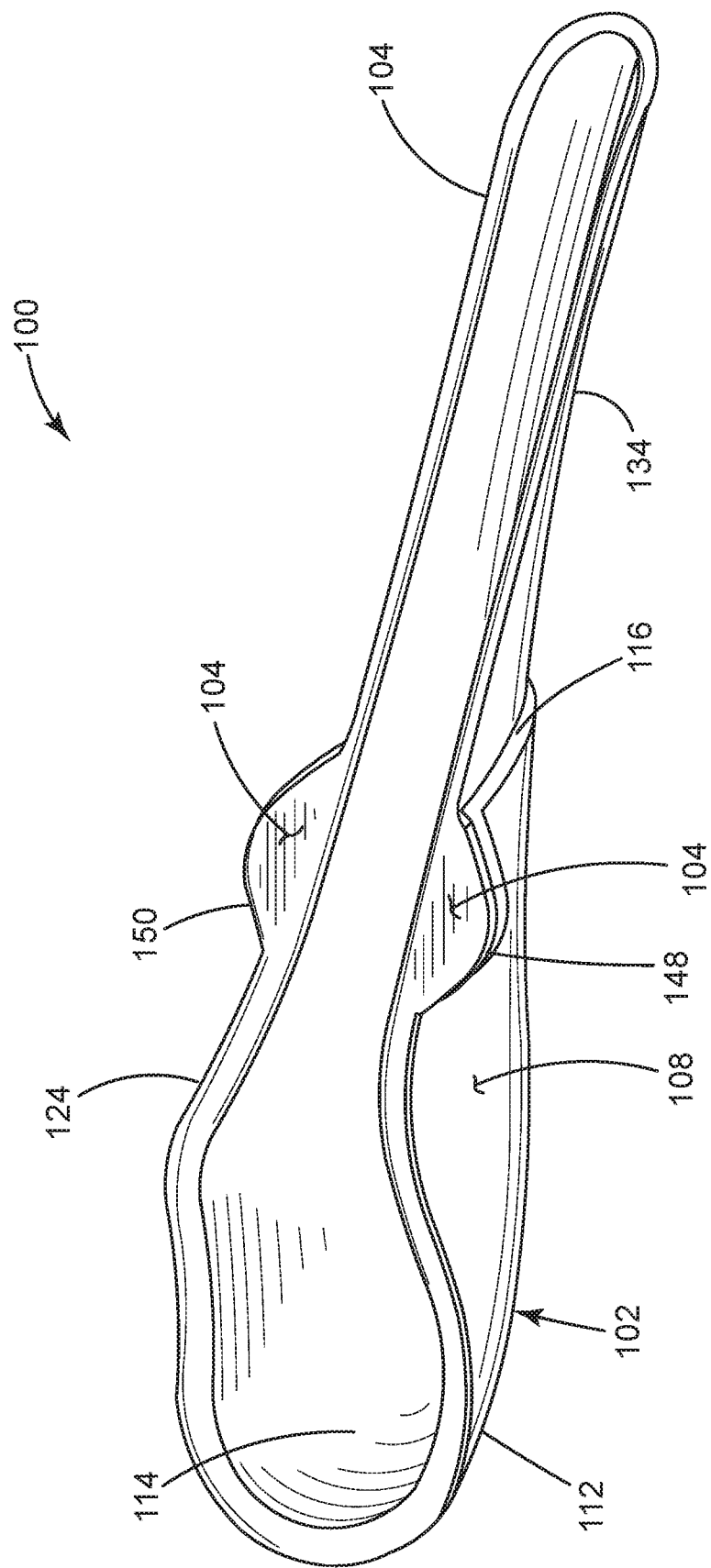
FIG. 1 depicts a perspective view of an example of a female urine device having a shell and an inner liner, wherein the inner liner includes a spout portion that is in an extended position, according to aspects described herein.
Figure 4:
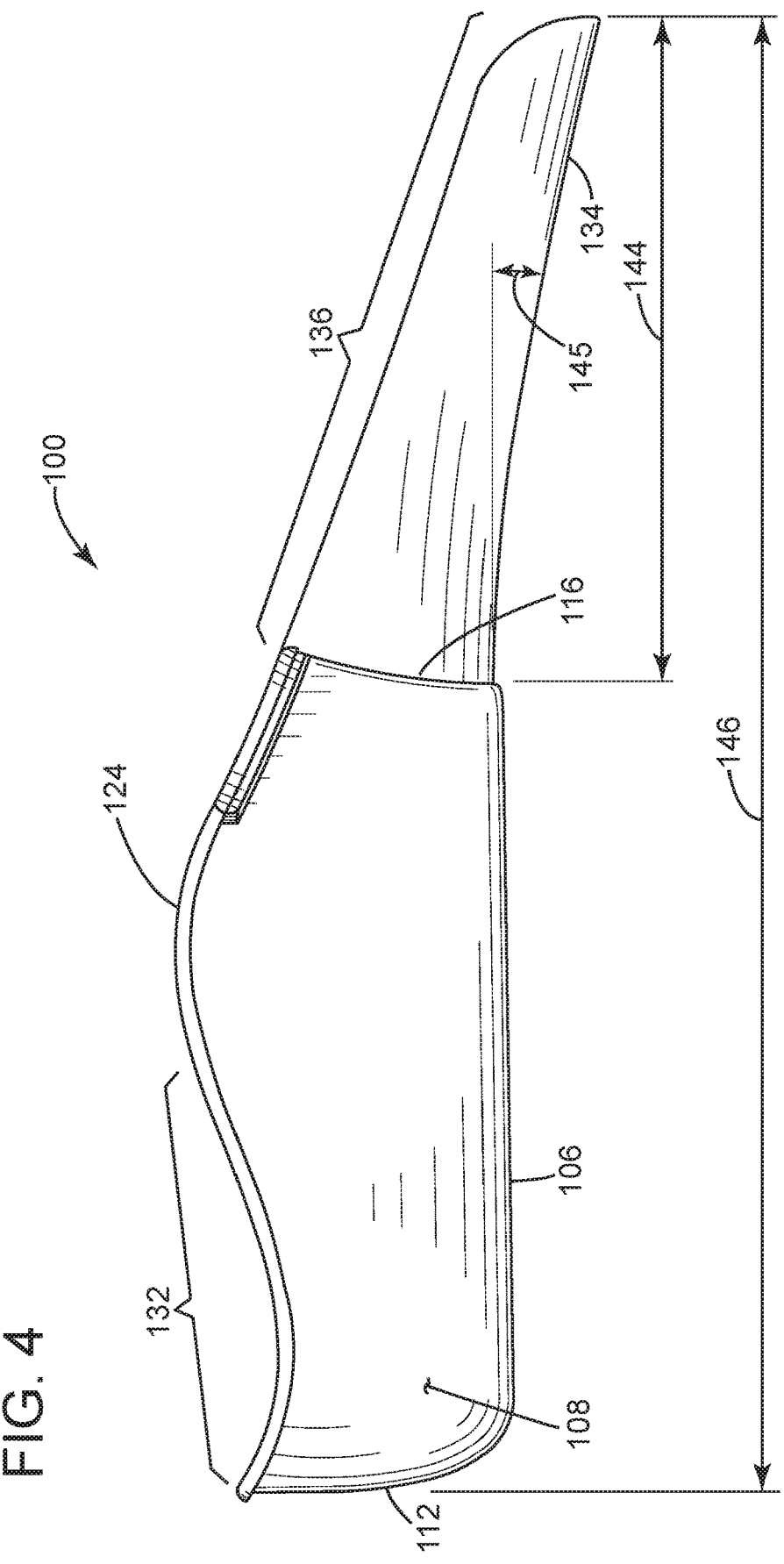
FIG. 4 depicts a side view of the example of the female urine device of FIG. 1 according to aspects described herein.

FIG. 7 depicts a perspective view of an example of a female urine device with its spout portion in a folded position within an inner chamber of the female urine device according to aspects described herein; and FIG. 8 depicts a perspective view of an example of a female urine device with its spout portion in a folded position against a bottom wall of the female urine device according to aspects described herein.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "substantially", "approximately", "about", "relatively," or other such similar terms that may be used throughout this disclosure, including the claims, are used to describe and account for small fluctuations, such as due to variations in processing from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

FIGS. 1-4 illustrate various examples of a female urine device in an extended position according to aspects described herein. FIG. 5 illustrates an example of a female urine device having thumb rests operable as fulcrums to enable a female to leverage the device into an anatomic sealing engagement with the female's genitalia according to aspects described herein. Finally, FIGS. 7-8 illustrate various examples of a female urine device in at least one folded position according to aspects described herein.

Referring to FIGS. 1-4, a perspective view (FIG. 1), a top view (FIG. 2), a bottom view (FIG. 3) and a side view (FIG. 4) of an example of a female urine device 100 is presented according to aspects described herein. The urine device 100 includes a shell 102 and a resilient liner 104.

The shell 102 includes a bottom wall 106, a first sidewall 108, a second sidewall 110 and a rear wall 112 (the walls being best seen in FIG. 3). The walls 106, 108, 110, 112 are integrally connected together to define a trough shaped inner chamber 114 (best seen in FIG. 2).

The shell 102 includes a generally U-shaped forward opening 116. The opening 116 is defined by a forward end 118 of the bottom wall 106, a forward end 120 of the first sidewall 108 and a forward end 122 of the second sidewall 110 (best seen in FIG. 3).

The shell 102 also includes an upper rim 124. The rim 124 is defined by an upper end 126 of the rear wall 112, an upper end 128 of the first sidewall 108 and an upper end 130 of the second sidewall 110 (best seen in FIG. 2). As will be discussed in greater detail herein, a portion of the rim 124 includes a concave shaped curve 132 (best seen in FIG. 4) that is designed to anatomically fit against a female's genitalia. More specifically, the rim 124 includes a pair of concave shaped curves 132 that are disposed along a portion of the upper ends 128, 130 of each sidewall 108, 110 respectively.

The shell 102 is tough enough such that it will not collapse during use. More specifically, it will not collapse when enough pressure is applied to the shell to assure a leak proof fit with a female's genitalia during use. Moreover, the shell 102 may be tough in that it may have the quality of being strong or firm in texture, but flexible and not brittle. Accordingly, the shell may be flexible enough to allow a female user to spread the upper ends 128 of the first side wall 108 and the upper end 130 of the second side wall 110 apart in order to customize the fit of the female urine device 100 to different body types when in use. Additionally, the shell may be durable enough such that it will resist cracking when inadvertently stepped on or dropped. When used, the trough shaped inner chamber 114 of the shell 102 is sized to fit over a female's urethra (including a female's urethral orifice) and to receive urine therefrom without spillage.

The shell 102 may be composed of a variety of materials. For example, the shell 102 may be composed of a non-absorbent plastic, metal, glass, carbon, cellulose, ceramic, biodegradable material or the like. Additionally, the shell 102 may be impregnated with anti-microbial additives to reduce the potential for bacterial growth in the liner. Further, the shell 102 may be impregnated with ultraviolet (UV) stabilizer additives to help prevent device degradation. Also, hydrophobic additives may be impregnated into the shell 102 to help make the shell non-porous or to enhance the shell's properties to shed liquids.

The resilient liner 104 is disposed on, and may cover, the entire inner chamber 114 (best seen in FIG. 2). The liner 104 also may cover the upper rim 124 of the shell 102. The liner 104 extends forward past the forward opening 116 of the shell 102 to form a spout portion 134 of the liner 104.

As will be discussed in greater detail herein, the spout portion 134 has an extended position and at least one folded position. More specifically, the spout portion 134 has an extended position 136 (best seen in FIG. 4) that the spout portion 134 is positioned in when the female urine device 100 is in use. Also more specifically for the examples illustrated herein, the spout portion 134 has at least three folded positions 190, 192, 194 (best seen in FIGS. 7, 8 and 9 respectively) that the spout portion 134 may be positioned in when the female urine device 100 is being stored.

When the spout portion 134 is in its extended position 136, the spout portion 134 has a length 144 that is greater than 40% of an extended length 146 of the female urine device 100. The reason that the length 144 of the spout portion 134 in its extended position 136 can be so long relative to the extended length 146 of the device 100, is that the shell 102 supports the spout portion 134 of the liner 104.

As such, the spout portion 134 is advantageously resilient and flexible enough to be folded into a variety of folded positions 190, 192, 194 for compact storage. However due in no small part to the added support of the shell 102, the spout portion 134 is also advantageously rigid enough in its extended position 136 to direct urine flow well away from a female's body without splashing urine on a female's clothing. For example, if a female urine device 100 is designed to have an overall length of about 9 inches, the spout portion 134 may be up to 4 inches long and longer in its extended position 136 in order to direct urine 178 away from the body 160 when in use (best seen in FIG. 5B).

Additionally, when the spout portion 134 is in its extended position 136, the floor of the spout portion 134 forms a downward sloping angle 145 relative to the bottom wall 106 of the shell 102. The downward sloping angle 145 is preferably within a range of about 5 degrees to 20 degrees. More preferably the angle 145 is within a smaller range of about 10 degrees to 15 degrees. The downward sloping angle 145 aids in directing the urine flow down and away from a female's body without splashing urine on a female's clothing.

The resilient liner 104 may be composed of a variety of materials. For example, the liner 104 may be composed of a non-absorbent, non-porous plastic, urethane, cellulose, carbon, silicone, rubber, biodegradable material or the like. Additionally, the liner 104 may be impregnated with anti-microbial additives to reduce the potential for bacterial growth in the liner. Further, the liner 104 may be impregnated with ultraviolet (UV) stabilizer additives to help prevent degradation. Also, hydrophobic additives may be impregnated into the liner 104 to help make the liner non-porous or to enhance the shell's properties to shed liquids.

At least one thumb rest 148 is disposed on a sidewall 108 of the shell 102 and extends perpendicularly therefrom. As will be discussed in greater detail herein, the at least one thumb rest 148 is sized to receive a thumb of a female and is advantageously operable as a fulcrum to enable the female to leverage the rim 124 of the shell 102 into sealing engagement with the female's genitalia when the female urine device 100 is in use. Moreover, the additional surface area of the thumb rest 148 provides comfort to the user's thumb when applying pressure.

More specifically for the examples illustrated herein, there is a pair of first 148 and second 150 thumb rests, wherein the first thumb rest 148 is disposed on the first sidewall 108 and the second thumb rest 150 is disposed on the second sidewall 110. The pair of thumb rests 148, 150 may be disposed on the rim 124 and may be adjacent the forward opening 116 of the shell 102. The pair of thumb rests 148, 150 may be composed of the same material as that of the shell 102.

The liner 104, as illustrated in these examples, may also cover the thumb rests 148, 150 (best seen in FIG. 2). This has the advantageous effect of providing a more comfortable and more non-slip surface relative to the material of the shell 102. As such, the thumb of a female would be less prone to slipping off of the thumb rests 148, 150 during use.

Additionally, the thumb rests 148, 150 act as a reference guide for consistent proper placement against a female's body. More specifically (as best seen in FIG. 5B), when the female urine device 100 is in use, the thumb rests 148, 150 are positioned on the forward end of the shell 102 and the shell is sized such that when the thumb rests 148, 150 are in front of (or anterior to) a female's body, the rear wall 112 of the shell 102 is positioned behind (or posterior to) the urethral orifice 176.

In this specific example, the liner 104 includes a pair of tabs 149 (best seen in FIG. 3) that extend downward into through-holes 151 that are disposed in the thumb rests 148, 150. The tabs 149 help to properly position the liner 104 relative to the tabs 148, 150 and the shell 102. The tabs 149 also help to further fix the position of the liner 104 against the thumb rests 148, 150 during use of the female urine device 100.

Figure 5A:
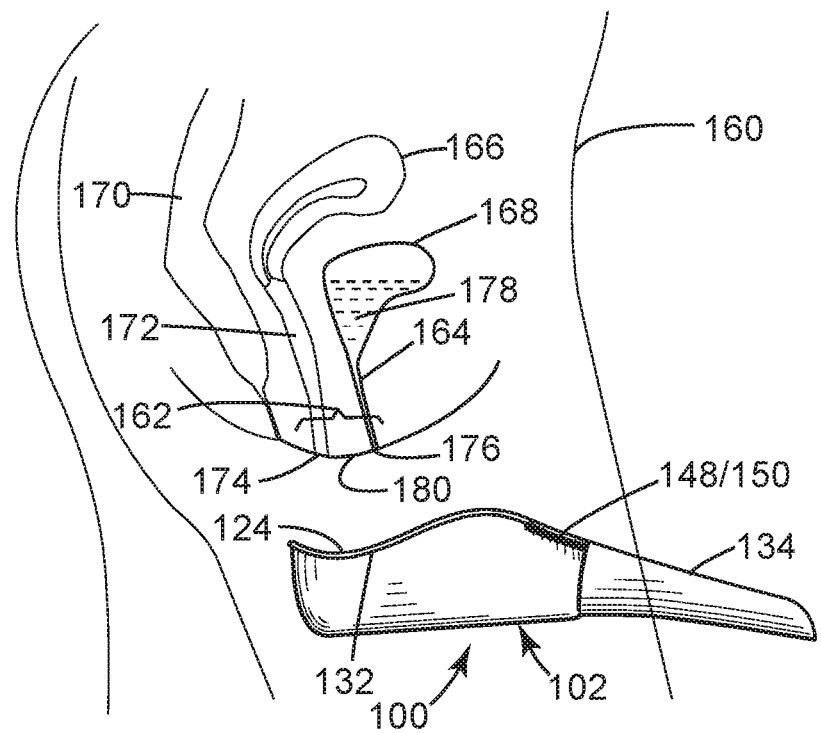
FIG. 5A, depicts a perspective view of an example of a female urine device positioned such that it is about to be engaged against a female's body according to aspects described herein.
Figure 5B:
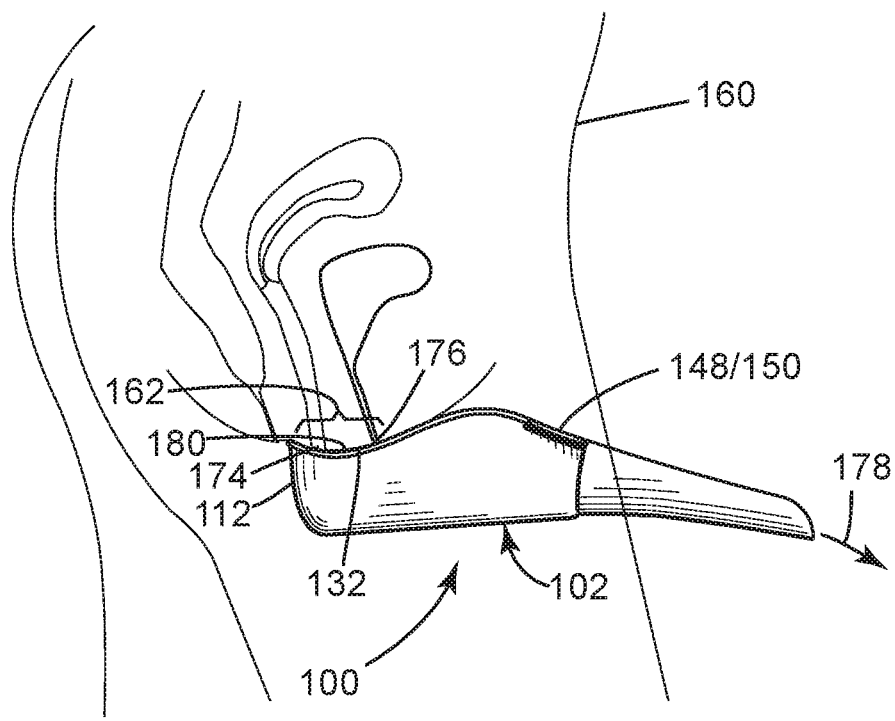
FIG. 5B depicts a perspective view of an example of the female urine device of FIG. 5A positioned against a female's body according to aspects described herein.

Referring to FIG. 5A, a perspective view of an example of the female urine device 100 positioned such that it is about to be engaged against a female's body 160 according to aspects described herein is presented. The shell 102 of the female urine device 100 is sized such that when the upper rim 124 is engaged with the female's genitalia 162, the liner covered inner chamber 114 (best seen in FIG. 1) is positioned to receive urine from the female's urethral orifice 176 and the pair of thumb rests 148, 150 are positioned in front of (or anterior to) the female's body 160.

The female uterus 166 is the hollow muscular organ positioned in the female's body 160 between the bladder 168 and rectum 170, and is part of the female's reproductive system. The uterus 166 connects through the vaginal canal 172 to the vaginal opening 174, which is part of the female's external genitalia 162.

The urethral orifice 176 is positioned anterior to (or in front of) the vaginal opening 174. Urine 178 is stored in the bladder 168 and flows through the urethra 164, where it is ejected out of the urethral orifice 176 during urination.

The area of a female's body which includes the female's genitalia 162 forms a convex shaped curvature 180 due, in large part, to the shape of the female's pelvis (not shown). The concave curve 132 of the female urine device 100 is designed to anatomically fit against the convex curvature 180 of the female's body 160 to provide a more comfortable fit and to enable a leak resistant seal with minimal pressure. Moreover, the thumb rests 148, 150 are positioned forward of the concave curve 132 so that the thumb rests 148, 150 do not interfere with the fit of the concave curve 132 to the convex curvature 180 of female's genitalia 162.

By way of example, the concave curve 132 may have a radius of curvature that is within a range of 2.0 inches to 3.25 inches. More preferably the concave curve 132 may have a radius of curvature that is within a smaller range of 2.15 inches to 2.85 inches. These examples of ranges of radii will, in most cases, enable the female urine device 100 to anatomically fit against the corresponding convex curvature 180 of the female's body 160.

Additionally by way of example, the concave shaped curve 132 may form an arc that is within an angular range of between 25 degrees and 60 degrees. More preferably the curve 132 may form an arc that is within an angular range of between 40 degrees and 60 degrees.

Referring to FIG. 5B, a perspective view of an example of the female urine device 100 positioned against a female's body 160 according to aspects described herein is presented. When the urine device 100 is in use, the upper rim 124 is operable to engage a female's genitalia 162. The liner covered inner chamber 114 (best seen in FIG. 1) is operable to receive urine 178 from the female's urethral orifice 176. Further, the spout portion 134 is in an extended position 136 to direct the urine 178 away from the female's body 160.

To engage the female urine device 100 during use, a female may use the thumb rests 148, 150 as reference points in front of the female's body 160 to properly position the device 100. For example, the thumb rests 148, 150 may be positioned on the shell 102 proximate its forward opening 116 and forward of its concave curve 132. The shell may be sized such that, when a female positions the thumb rests 148, 150 in front of her body, the rear wall 112 of the shell 102 will be located behind her urethral orifice and the concave curve 132 will anatomically fit against the convex curve 180 of the female's genitalia 162. The liner covered inner chamber 114 of the shell 102 is placed under the urethral orifice 176, so that urine 178 flows directly into the chamber 114. When so placed, the rim 124 on the upper end of the rear wall 112 is generally positioned under, or near, the vaginal opening 174 and the thumb rests 148, 150 are accessible in front of the female's clothing.

By placing her thumbs (not shown) on the thumb rest 148, 150 and cupping the bottom wall 106 of the shell 102 with her fingers (not shown), a female may utilize the thumb rests as a fulcrum to leverage the rim 124 of the shell 102 into sealing engagement with the female's genitalia 162. Accordingly, the rim 124 on the rear wall 112 is pushed upwards to seal against the genitalia 164 while the spout portion 134 is pushed downward to aim the flow of urine 178 away from the body 160. Advantageously, the proportionally long length 144 of the spout portion 134 in its extended position 136 (e.g., more than 40% of the extended length 146 of the female urine device 100) enables the flow of urine 178 to be directed away from the female's body without inadvertently splashing on her clothing. Additionally, the presence of hydrophobic additives enhances the device's ability to not absorb urine and to shed urine more quickly.

When the urination process is completed, the rim 124 on the upper end of the rear wall 112 of the female urine device 100 is operable to act as a squeegee to wipe the genitalia 162 clean of urine. This may be accomplished by gently pulling the female urine device 100 forward (or anteriorly) while maintaining pressure of the rim 124 of the rear wall 112 against the body 160. The soft resilient liner 104 covering the rear wall rim 124 will wipe urine off of the genitalia 162 in a squeegee like fashion. The remaining drops of urine may then be shaken off of the urine device 100. Additionally, the antimicrobial additives that have been impregnated into the liner 104 will work to reduce the potential for bacterial growth on the liner 104 during and after the process of wiping the female genitalia 162.

Figure 6:
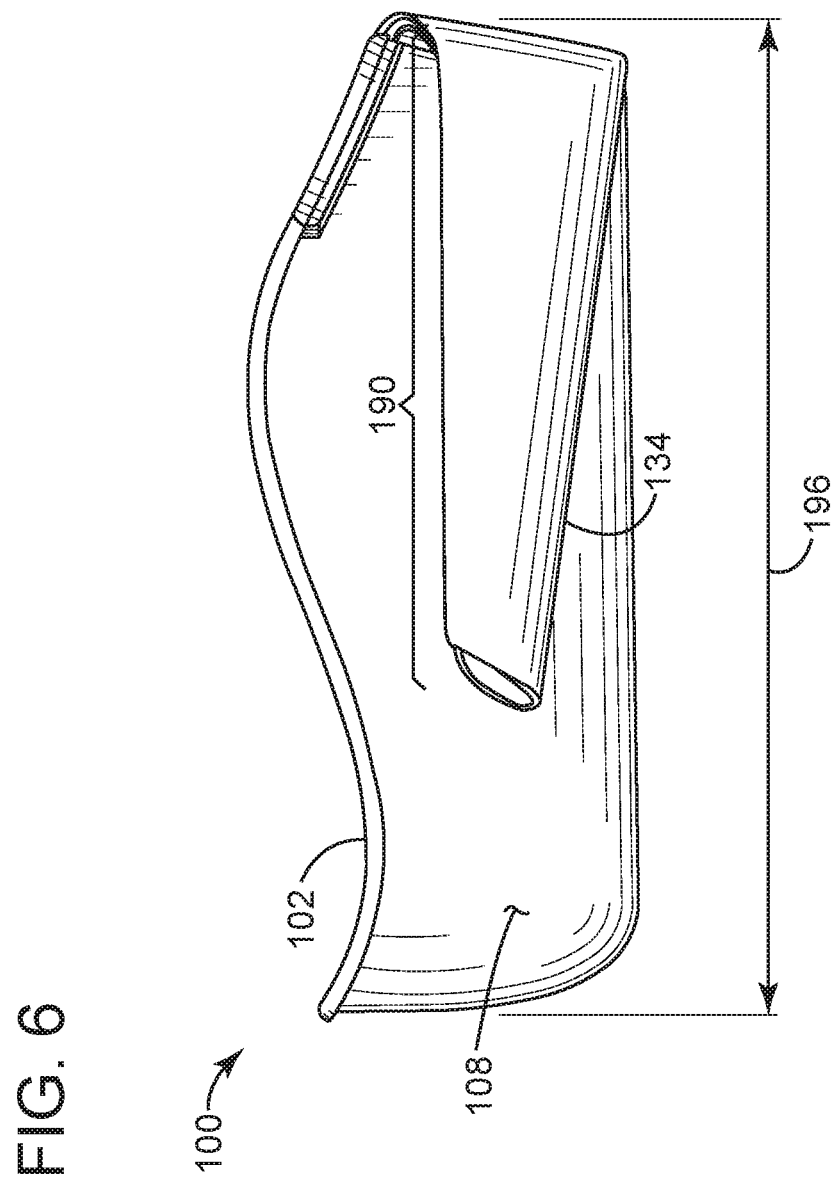
FIG. 6 depicts a perspective view of an example of a female urine device with its spout portion in a folded position against a sidewall of the female urine device according to aspects described herein.

Referring to FIGS. 6, 7 and 8, various examples of a female urine device 100 with its spout portion 134 in a folded position are presented according to aspects described herein. More specifically, FIG. 6 depicts a perspective view of an example of a female urine device 100 with its spout portion 134 in a first folded position 190 against a sidewall 108 of the female urine device 100. Also, FIG. 7 depicts a perspective view of an example of a female urine device 100 with its spout portion 134 in a second folded position 192 within an inner chamber 114 of the female urine device 100. Further, FIG. 8 depicts a perspective view of an example of a female urine device 100 with its spout portion 134 in a third folded position 194 against a bottom wall 106 of the female urine device 100. The various folded positions 190, 192, 194 enable the female urine device 100 to advantageously be more compactly stored when not in use.

When the urine device 100 is not in use, the spout portion 100 is operable to be folded into at least one folded position 190, 192, 194 against the shell 102 for purposes of storage of the urine device. When the spout portion 134 is in its folded position 190, 192, 194, the female urine device 100 has a folded length 196 that is less than 67% of its extended length 146.

The reason that the folded length 196 is small relative to the extended length 146 (e.g., less than 67% of the extended length 146) of the urine device 100 is because of the resiliency and the proportionally long length 144 of the spout portion 134. That is, the resiliency of the spout portion 134 allows it to be folded against the shell 102. Further the proportionally long length of the spout portion 134 enables a significant difference between the extended length 136 and folded length 196 of the device 100. For example, if a female urine device 100 is designed to have an overall length of about 9 inches, the spout portion 134 may be up to 4 inches long and longer in order to direct urine away from the body when in use. However, when the spout portion 134 is folded against the shell 102, the folded length will be reduced to about 5.5 inches. Accordingly the female urine device 100 will be long enough to prevent urine from splashing onto a females clothing when in use, but will also be very compact for storage when not in use.

Referring to FIG. 6 more specifically, an example of the female urine device 100 with its spout portion 134 in the first folded position 190 against a sidewall 108, 110 of the female urine device 100 is illustrated. The spout portion 134 may be folded against either the first side wall 108 or the second side wall 110.

Referring to FIG. 7 more specifically, an example of the female urine device 100 with its spout portion 134 in a second folded position 192 within the liner covered inner chamber 114 of the female urine device 100 is illustrated. The spout portion 134 may be fully enclosed within the inner chamber 114.

Referring to FIG. 8 more specifically, an example of the female urine device 100 with its spout portion 100 in the third folded position 194 against the bottom wall 106 of the female urine device 100 is illustrated. Advantageously, when the spout portion 134 is folded against the bottom wall 106, the spout portion 134 alone is operable to retain itself in its folded position 194 without snapping back into its extended position 136. Though three folded positions 190, 192, 194 of the spout 134 have been illustrated therein, other folded positions may also be used to reduce the overall length of the female urine device 100 when not in use.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. A female urine device, comprising:
a shell comprising:

a bottom wall, a first sidewall, a second sidewall and a rear wall integrally connected to define a trough shaped inner chamber,
a forward opening defined by forward ends of the walls, and
an upper rim defined by upper ends of the walls, the upper rim extending from an upper end of the rear wall to the forward opening, wherein the forward opening defines an open end of the upper rim;
a resilient liner disposed on the inner chamber, the liner extending forward past the forward opening of the shell to form a spout portion of the liner; and
at least one thumb rest disposed on a sidewall of the shell and extending perpendicularly therefrom, the at least one thumb rest being disposed adjacent to the forward opening of the shell, the at least one thumb rest sized to receive a thumb of a female and being operable as a fulcrum to enable the female to leverage the rim of the shell into sealing engagement with the female's genitalia when the female urine device is in use.

2. The female urine device of claim 1, wherein the at least one thumb rest is a pair of first and second thumb rests, wherein the first thumb rest is disposed on the first sidewall and the second thumb rest is disposed on the second sidewall.

3. The female urine device of claim 2, wherein the pair of thumb rests are disposed on the rim and are adjacent the forward opening of the shell.

4. The female urine device of claim 2, wherein:
when the urine device is in use, the upper rim is operable to engage a female's genitalia, the liner covered inner chamber is operable to receive urine from the female's urethral orifice and the spout portion is in an extended position to direct the urine away from the female's body; and
when the urine device is not in use, the spout portion is operable to be folded into at least one folded position against the shell for purposes of storage of the urine device.

5. The female urine device of claim 4, wherein the at least one folded position of the spout portion comprises one of:
a first folded position, wherein the spout portion is disposed against a side wall of the urine device while the resilient liner remains disposed on the inner chamber; and
a second folded position, wherein the spout portion is disposed within the liner covered inner chamber of the urine device while the resilient liner remains disposed on the inner chamber.

6. The female urine device of claim 4, wherein the at least one folded position of the spout portion comprises a folded position, wherein the spout portion is disposed against the bottom wall of the urine device while the resilient liner remains disposed on the inner chamber.

7. The female urine device of claim 6, wherein when the spout portion is folded against the bottom wall, the spout portion alone is operable to retain itself in its folded position without reverting back into its extended position.

8. The female urine device of claim 1, wherein a portion of the upper rim has a concave shaped curve designed to anatomically fit against the female's genitalia.

9. The female urine device of claim 2, wherein the shell is sized such that when the upper rim is engaged with the female's genitalia, the liner covered inner chamber is positioned to receive urine from the female's urethral orifice and the pair of thumb rests are positioned in front of the female's body.

10. The female urine device of claim 1, wherein:
when the spout portion is in its extended position, the spout portion has a length that is greater than 40% of an extended length of the female urine device; and
when the spout portion is in its folded position, the female urine device has a folded length that is less than 67% of its extended length.

11. A female urine device, comprising:
a shell comprising:
a bottom wall, a first sidewall, a second sidewall and a rear wall integrally connected to define a trough shaped inner chamber,
a forward opening defined by forward ends of the walls, and
an upper rim defined by upper ends of the walls;
a resilient liner disposed on the inner chamber, the liner extending forward past the forward opening of the shell to form a spout portion of the liner, the spout portion having an extended position and at least one folded position;
wherein when the urine device is in use, the upper rim is operable to engage a female's genitalia, the liner covered inner chamber is operable to receive urine from the female's urethral orifice and the spout portion is in its extended position to direct the urine away from the female's body; and
wherein when the urine device is not in use, the spout portion is operable to be folded into its at least one folded position against the inner chamber, while the resilient liner remains disposed on the inner chamber, for purposes of storage of the urine device.

12. The female urine device of claim 11, wherein the at least one folded position of the spout portion comprises one of:
a first folded position, wherein the spout portion is disposed against a side wall of the urine device; and
a second folded position, wherein the spout portion is disposed within the liner covered inner chamber of the urine device.

13. The female urine device of claim 11, wherein the at least one folded position of the spout portion comprises a third folded position, wherein the spout portion is disposed against the bottom wall of the urine device.

14. The female urine device of claim 13, wherein when the spout portion is disposed against the bottom wall, the spout portion alone is operable to retain itself in its folded position without reverting back into its extended position.

15. The female urine device of claim 11, wherein a portion of the upper rim has a concave shaped curve designed to anatomically fit against the female's genitalia.

16. The female urine device of claim 11, comprising at least one thumb rest disposed on a sidewall of the shell and extending perpendicularly therefrom, the at least one thumb rest sized to receive a thumb of the female and being operable as a fulcrum to enable the female to leverage the rim of the shell into sealing engagement with the female's genitalia when the female urine device is in use.

17. The female urine device of claim 16, wherein the at least one thumb rest is a pair of first and second thumb rests, wherein the first thumb rest is disposed on the first sidewall and the second thumb rest disposed on the second sidewall.

18. The female urine device of claim 17, wherein the pair of thumb rests are disposed on the rim and are adjacent the forward opening of the shell.

19. The female urine device of claim 18, wherein the shell is sized such that when the upper rim is engaged with the female's genitalia and the liner covered inner chamber is positioned to receive urine from the female's urethral orifice, the pair of thumb rests are positioned in front of the female's body.

20. The female urine device of claim 11, wherein:
when the spout portion is in its extended position, the spout portion has a length that is greater than 40% of an extended length of the female urine device; and
when the spout portion is in its folded position, the female urine device has a folded length that is less than 67% of its extended length.

21. A female urine device, comprising:
a shell comprising:
a bottom wall, a first sidewall, a second sidewall and a rear wall integrally connected to define a trough shaped inner chamber,
a forward opening defined by forward ends of the walls, and
an upper rim defined by upper ends of the walls, the upper rim extending from an upper end of the rear wall to the forward opening, wherein the forward opening defines an open end of the upper rim;
a resilient liner disposed on the inner chamber, the liner extending forward past the forward opening of the shell to form a spout portion of the liner; and
at least one thumb rest disposed on the rim of the shell and extending perpendicularly therefrom, the at least one thumb rest also disposed adjacent to the forward opening, the at least one thumb rest sized to receive a thumb of a female and being operable as a fulcrum to enable the female to leverage the rim of the shell into sealing engagement with the female's genitalia when the female urine device is in use;
wherein a portion of the upper rim has a concave shaped curve designed to anatomically fit against the female's genitalia.

22. The female urine device of claim 21, wherein the concave shaped curve has a radius that is within a range of 2.15 inches to 2.85 inches.

23. The female urine device of claim 21, wherein the at least one thumb rest comprises a first thumb rest disposed on a first sidewall of the shell and a second thumb rest disposed on a second sidewall of the shell, the first and second thumb rests positioned proximate the forward opening of the shell and forward of the concave shaped curve of the shell.

24. The female urine device of claim 21, wherein the resilient liner has an extended position and at least one folded position.

25. The female urine device of claim 1, wherein the spout portion of the liner forms an open trough.

26. The female urine device of claim 1, wherein the liner is permanently fixed to the shell.

27. The female urine device of claim 1, wherein the liner is impregnated with anti-microbial additives to reduce the potential for bacterial growth in the liner.

28. The female urine device of claim 1, wherein the liner is impregnated with ultraviolet stabilizer additives to prevent device degradation.

* * * * *